US012396647B2

(12) United States Patent
Danesh

(10) Patent No.: US 12,396,647 B2
(45) Date of Patent: Aug. 26, 2025

(54) SPECTROGRAPHIC TOOTH EVALUATION SYSTEM

(71) Applicant: Ali Danesh, San Diego, CA (US)

(72) Inventor: Ali Danesh, San Diego, CA (US)

(*) Notice: Subject to any disclaimer, the term of this patent is extended or adjusted under 35 U.S.C. 154(b) by 63 days.

(21) Appl. No.: 18/057,338

(22) Filed: Nov. 21, 2022

(65) Prior Publication Data

US 2023/0270341 A1 Aug. 31, 2023

Related U.S. Application Data

(63) Continuation-in-part of application No. 17/929,861, filed on Sep. 6, 2022, now abandoned.

(60) Provisional application No. 63/241,218, filed on Sep. 7, 2021.

(51) Int. Cl.
*A61B 5/00* (2006.01)
*A46B 15/00* (2006.01)

(52) U.S. Cl.
CPC ........ *A61B 5/0088* (2013.01); *A46B 15/0034* (2013.01); *A61B 5/0071* (2013.01); *A61B 5/742* (2013.01); *A46B 2200/1066* (2013.01); *A61B 5/0075* (2013.01); *A61B 5/4547* (2013.01)

(58) Field of Classification Search
None
See application file for complete search history.

(56) References Cited

U.S. PATENT DOCUMENTS

| 7,223,270 B2 | 5/2007 | Altshuler |
| 11,311,363 B2 | 4/2022 | Kawabata |
| 2011/0102566 A1* | 5/2011 | Zakian ................. A61B 5/0086 348/66 |
| 2013/0203008 A1 | 8/2013 | Kressman |
| 2015/0010878 A1* | 1/2015 | Seibel ................. A61B 5/0071 433/215 |
| 2016/0287084 A1* | 10/2016 | Vermeulen ........... A61C 17/225 |
| 2019/0328234 A1* | 10/2019 | Seibel ................ A61B 5/14539 |

(Continued)

FOREIGN PATENT DOCUMENTS

| CN | 210301280 | 6/2019 | |
| EP | 4014838 A1 * | 6/2022 | ........... A61B 5/0075 |

OTHER PUBLICATIONS

Of Zezell et al., "Characterization of natural carious lesions by fluorescence spectroscopy at 405-nm excitation wavelength," (Nov. 1, 2007), Journal of Biomedical Optics, vol. 12, Issue 6, 064013. (Year: 2007).*

(Continued)

*Primary Examiner* — Jeffrey G Hoekstra
*Assistant Examiner* — Ashish S Jasani
(74) *Attorney, Agent, or Firm* — Scott C Harris, Esq

(57) ABSTRACT

A system that uses a spectrometer to evaluate dental enamel, and determines incipient tooth decay before it occurs. The system includes a housing, having at least one button, and at least one feedback mechanism on the housing which provides feedback to a user indicative of tooth decay. There is both an emitting laser on the housing and also a tooth bristle to brush user's teeth. A receiver which receives a reemission from the user's teeth that is produced by the laser light emitting from the emitting laser. This reemission is processed to determine an amount of tooth decay on a specific tooth. An output is created on the feedback mechanism whether a specific tooth has tooth decay.

5 Claims, 10 Drawing Sheets

(56) References Cited

U.S. PATENT DOCUMENTS

2021/0085168 A1  3/2021  Johnson
2021/0393026 A1  12/2021 Shubash
2024/0090772 A1* 3/2024  Subhash .......... A61B 1/000094

OTHER PUBLICATIONS

Thomas et al., "Clinical trial for detection of dental caries using laser-induced fluorescence ratio reference standard," (Mar. 1, 2010), Journal of Biomedical Optics, vol. 15, Issue 2, 027001. (Year: 2010).*
Ando et al., "Objective and quantitative assessment of caries lesion activity," (Nov. 2018), Journal of Dentistry, vol. 78, Nov. 2018, pp. 76-82. (Year: 2018).*
Optical PH Measurement System Using a Single Fluorescent Dye for Assessing Susceptibility To Dental Caries, Sharma, Jan. 8, 2019.
Oral B Cut Sheet.
Soniclean Brush Buddies.
Philips Sonicare Amazon Page.
Phylian Amazon Page.

* cited by examiner

SPECTROGRAPHIC TOOTH EVALUATION SYSTEM

This is a continuation in part of application Ser. No. 17/929,861, filed Sep. 6, 2022, the entire contents of which are herewith incorporated by reference which claims priority from provisional No. 63/241,218, filed Sep. 7, 2021, the entire contents of which are herewith incorporated by reference.

BACKGROUND

Diagnostic evaluation of teeth is typically done in a dentist's office by a dental professional. It is desirable to carry out dental evaluation as often as possible. However, surveys have shown 42% of Americans do not go to the dentist as regularly as they should, particularly during COVID-19. 36% of Americans with dental insurance still do not go to the dentist at least once a year, with this number jumping to 50% when looking at the lowest household incomes. My invention provides an at-home option, saving costs in reduced checkups as well.

Companies and devices have used light fluorescence as a method of detecting dental cavities.

DIAGNOdent—Uses a 655 nm laser to irradiate intraoral bacteria and records their fluorescence. The more fluorescence emitted by the bacteria the higher the value and indicative of dental issues. This system is expensive, and has issues with specificity/sensitivity. This system operates to analyze for bacteria fluorescence.

CamX Spectra—Uses a 405 nm lights to fluoresce enamel and bacteria. However, diagnostics are made through measuring the fluorescence of bacteria within cariogenic plaque which fluoresces in the red spectrum.

SoproLIFE—Uses 455 nm light to fluoresce bacteria color red and intraoral camera to show areas of decay within dentin.

These have been used in the professional dental space as diagnostic methods including visual-tactile, light fluorescence based devices.

Visual-tactile methods, including radiographs, can only detect incipient lesions once ≥30% demineralization has occurred, at which point it is too late for users to take steps and remineralize. Typical prior art which use fluorescence have investigated the bacterial fluorescence signals found in plaque.

SUMMARY OF THE INVENTION

The inventor recognized that there are a number of drawbacks with the current systems. Applicants believe that in the toothbrush and oral hygiene space, there are no products that are able to provide a monitoring or diagnostic aspect of dental caries or demineralization using the techniques described herein. There are no devices that offer a combination of the two at an affordable price for the average consumer.

The oral hygiene market has remained stagnant for a very long time. Inventions in consumer oral hygiene devices provide no effective functionality such as monitoring of pathologies, and have remained more or less the same for nearly 100 years.

The present application describes an app implementation and data storage would allow for a preventive dental environment for both the general practitioner dentist and their patient.

The app implementation would also allow 3-D models of users' mouths, highlighting specific parts of tooth that have been flagged as potential caries.

The present application describes techniques to look for dental changes, including structural changes in enamel of a user's teeth.

The system provides users feedback on where caries (cavities) are forming on their teeth at early reversible stages through the use of a hand-held, oral hygiene device, e.g, in one embodiment, a toothbrush.

Our toothbrush/device uses the science of QLF (Quantitative Light-induced Fluorescence) to detect demineralization within tooth enamel at the earliest stages. In an embodiment, this uses the loss of fluorescence intensity within enamel, quantified by an integrated spectrometer, to provide direct feedback to consumers much more cost effectively and portably.

An embodiment describes a toothbrush using QLF to evaluate changes in enamel structure in a user's tooth system.

Unlike the typical prior art which used fluorescence, the present application observes the fluorescence emitted by the enamel and dentin, using different wavelength and measurement technique than that in the prior art.

BRIEF DESCRIPTION OF THE DRAWINGS

In the Drawings:
the figures show aspects of the invention, and specifically.

DETAILED DESCRIPTION

The present application describes a specific toothbrush structure used as described herein, however is intended to cover not only the specific embodiments described herein, but the general concept of the invention, including all predictable modifications of these embodiments.

The physical structure of the invention includes a housing having an exterior case made of plastic or metal for an electric toothbrush or handheld device. Different buttons on the exterior housing are provided for detection mode and cleaning mode. An LED light on the bottom of the housing is used to give feedback to users.

Figure 1:
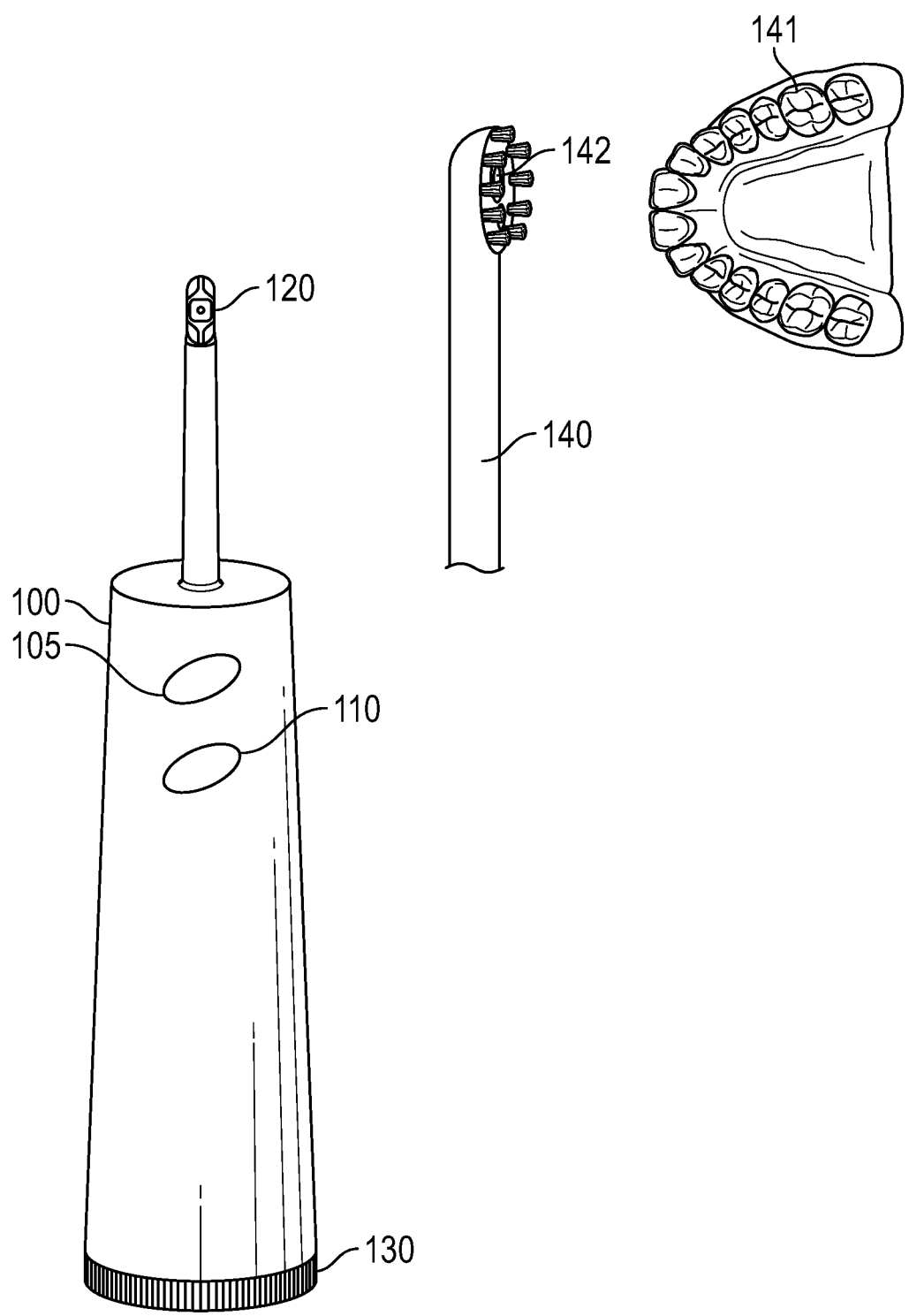
FIG. 1 shows the first embodiment of a toothbrush having the aspects of the present application.

A first embodiment, shown in FIG. 1 provides a housing 100 with the power button 105, and a detection button 110. A receiver module 120 is located at a top portion of the toothbrush. Feedback producing lights 130 can be on the bottom of the device and operate as described herein. A toothbrush bristle system 140 can be used to brush the user's teeth.

Figure 2:
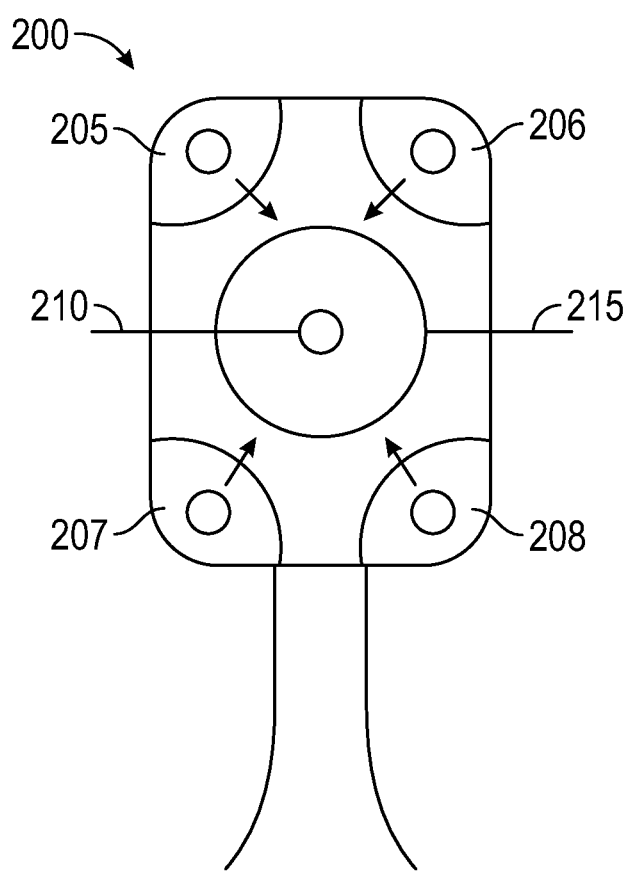
FIG. 2 shows the receiver outline.

FIG. 2 illustrates an outline of the actual receiver. This includes a fiber optic cable 200, covered with a 455 nm long pass filter. A number of 405 nm lasers 205, 206, 207, 208 surround the cable 200 forming the receiver and emit light towards the cable that eventually receives the light as described herein.

In operation, all of the parts to make the system operate, including a spectrometer, fiber optic cable, circuit board with processor, battery and filter are contained within the housing 100 of the device. In this first embodiment, the receiver 120 includes the 405 nm lasers and 455 nm filter. A battery, e.g., a lithium ion battery, operates the toothbrush.

A secondary tip portion 140 of the device/toothbrush is placed on top of the component containing the laser/LED diodes and the receiving end of the fiber optic cord as shown below. The component containing the 405 nm laser diode as well as one end of the fiber optic cable will be known as the receiving end. The secondary tip portion of the brush has bristles 142 that are used to brush the teeth.

Figure 4:
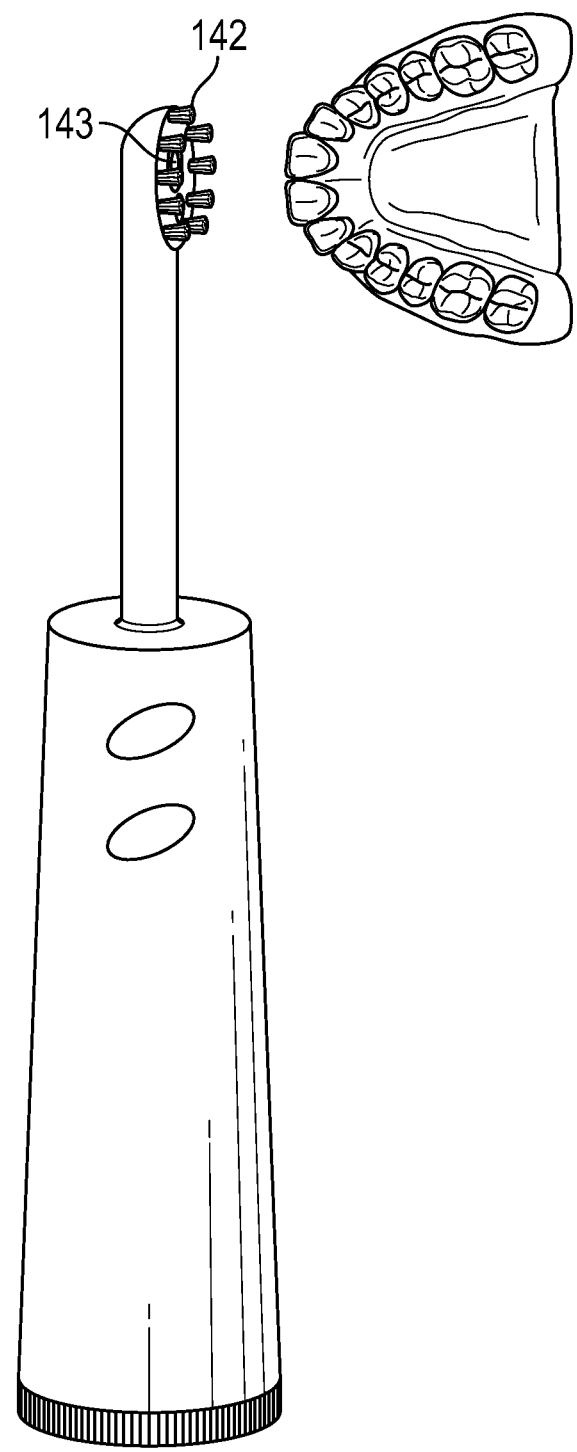
FIG. 4 shows a third embodiment.

In the embodiment of FIG. 4, there is a cutout 143 in the plastic casing where the laser/LED diodes and receiving end of the fiber optic cord are exposed.

In an alternative embodiment, shown in FIG. 1, there are no cutouts in the plastic casing, and access to the fiber optic and laser/LED diodes would only be possible through removal of the secondary tip.

Figure 3:
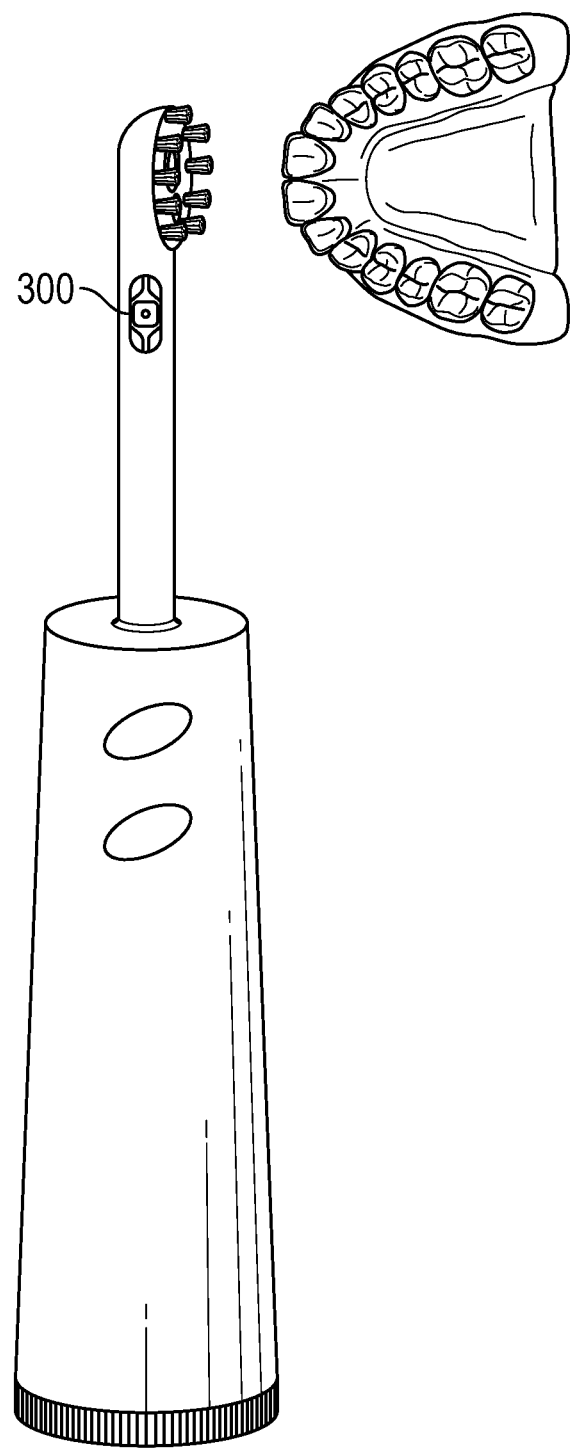
FIG. 3 shows a second embodiment.
Figure 5:
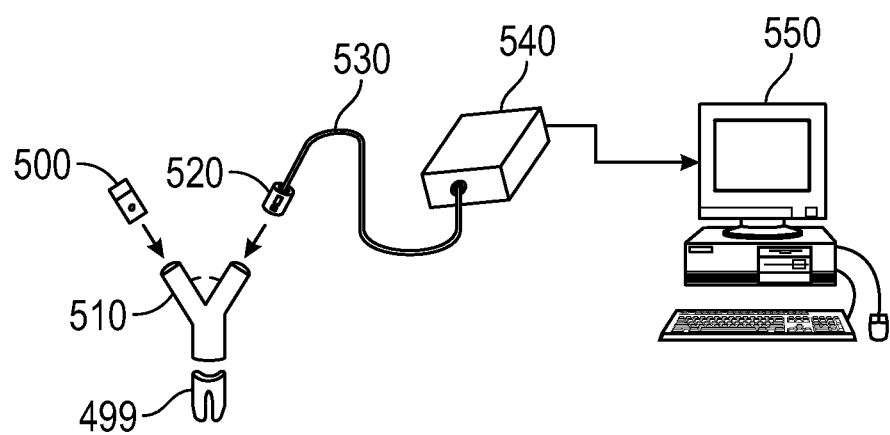
FIG. 5 shows a flow between the receiver and a computer.

Another embodiment shown in FIG. 3 exposes the receiving end through an opening 300 in the bristle handle. In operation, as described herein, the laser causes the enamel of the teeth to emit a wavelength, referred to herein as a reflection or re-emission, which is received by the receiver, FIG. 5 illustrates the different parts of the system. A laser 500 which can be one or more of the lasers described herein, is set to impinge on a tooth to be evaluated 499. The laser can be a 405 nm laser in an embodiment. This is done using a plastic holder 510, which can set the laser to impinge on the surface of the tooth at an angle between 45 and 55°.

The reflection from the tooth is received by a receiver 520 through a different arm of the plastic holder. The "reflection" is caused by the organic compounds within the tooth dentin, such as tryptophan, fluorophores, calcium-phosphate bonds, and the tooth enamel absorbing that laser light, and re-emitting the laser light at a different wavelength. The re-emission is in the 500 nm range. The receiver 520 is connected via a fiber optic cable 530 to a spectrometer device 540, in this embodiment a thunder optic spectrometer. In other embodiments, smaller spectrometers can be used. In one embodiment, the processing circuitry of a spectrometer can be included inside the housing 100. The output of the spectrometer is sent to a computer 550, which can be for example part of the user cellular phone, or can be within the circuitry.

Figure 6:
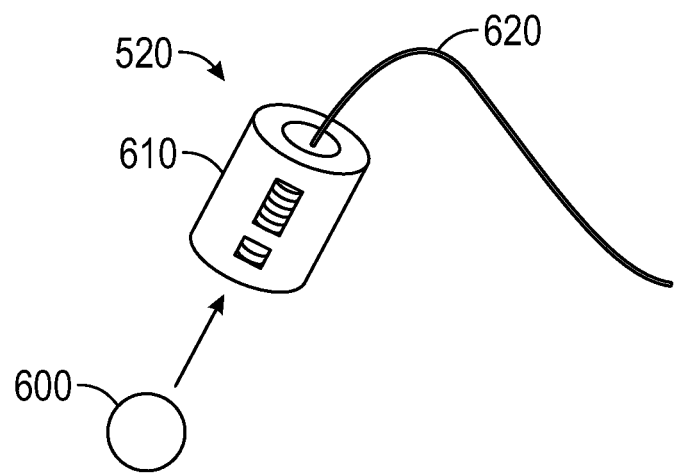
FIG. 6 shows a block diagram of the receiver.

A close-up of the receiver is shown in FIG. 6. A 455 nm long pass filter lens 600 is placed over a plastic casing 610. This has the effect to block the emitted light from the laser at 405 nm, and receive into the spectrometer 540 only the light that is re-emitted from the tooth. Blocking the emitted light from the receiver and receiving only the re-emitted light from the tooth provides a better indication of the health of the tooth. The output is directed to a fiber optic cable for example an SMA 905 fiber optic cable 620.

Figure 7:
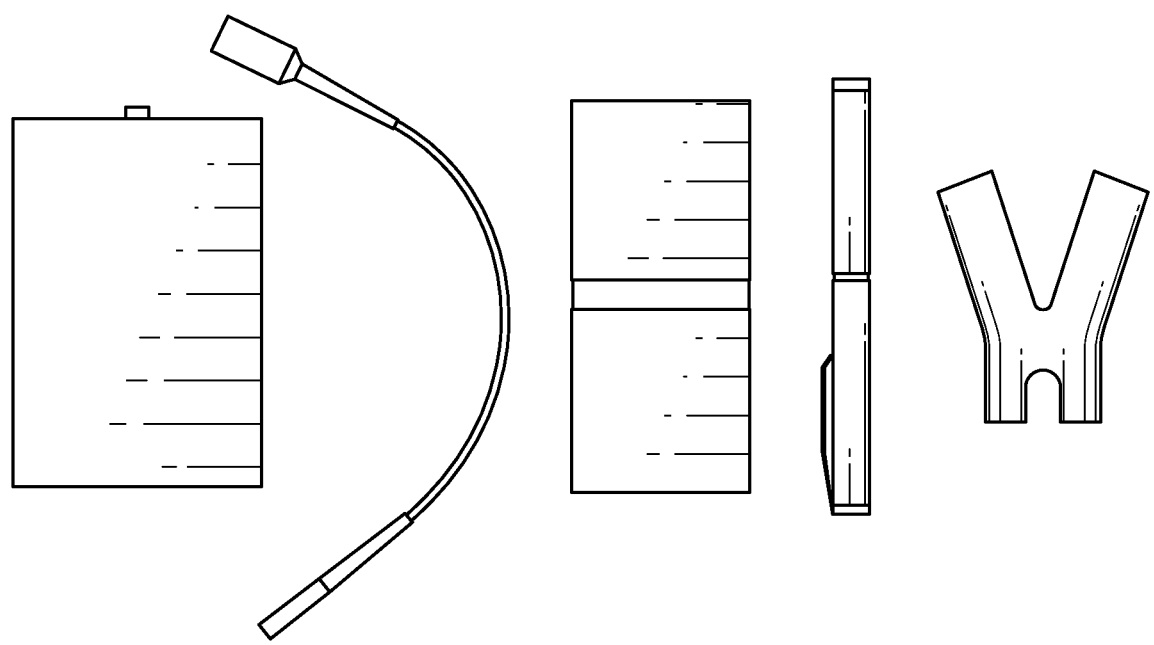
FIG. 7 shows the different structure.

FIG. 7 illustrates many of the parts which were used, including the spectrometer, the fiber optic cable, the long pass filter, the laser, and the plastic holder. The plastic casing can be 3D printed in one embodiment.

Figure 8A:
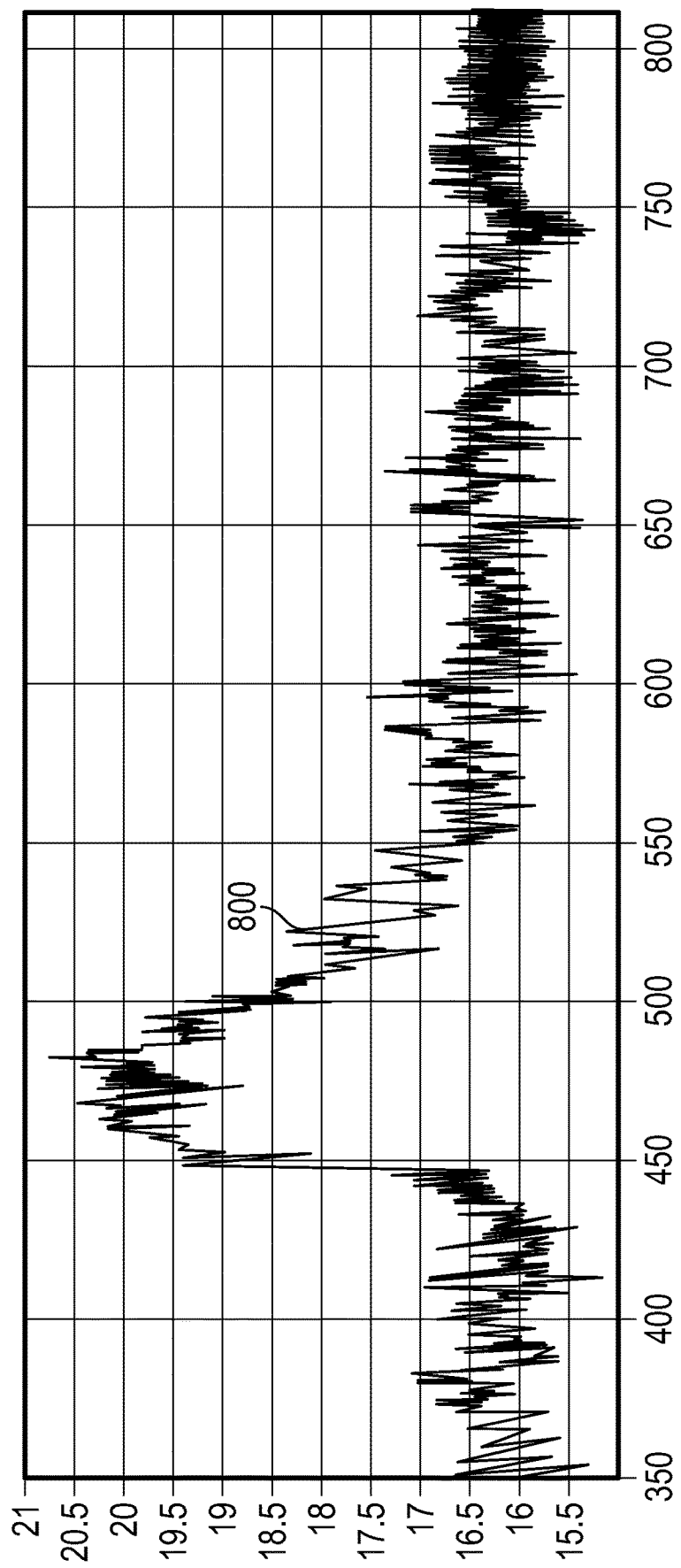
FIG. 8A shows a waveform with a detection peak for healthy enamel.

FIG. 8A illustrates an exemplary spectrograph of healthy enamel, showing the peak in the reflectivity, where the intensity is highest, being between 450-500 nm. The peak of this reflection forms a nicely shaped bell curve 800 with minimal noise. This nicely shaped bell curve indicates a healthy tooth. In general, a higher bell curve represents a healthier tooth.

Figure 8B:
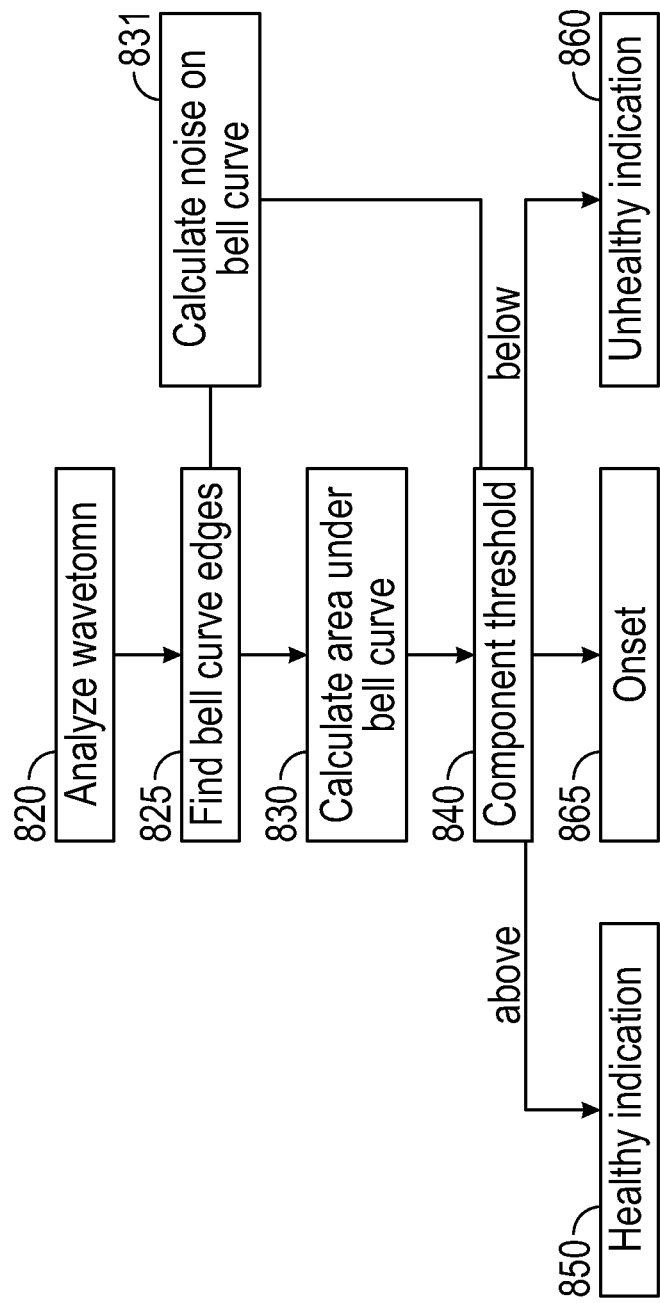
FIG. 8B shows a flowchart of operation of detecting the tooth health.

In an embodiment, the processor within the brush operates to characterize the bell curve 800 as illustrated in the flowchart of FIG. 8B. At 820, the processor operates to analyze the waveform. The waveform is graphed into a graph where for example the x-axis shows wavelength, and the y-axis shows intensity at that wavelength. This starts by finding the edges of the bell curve, e.g, by using predefined definitions for edge areas of the bell curve on the x axis which plots the wavelength of the received value. For example, the wavelength can extend between 450 and 500 nm. This can either be calculated, or set as the value at 825. After defining these edge areas, the processor calculates an area under the curve between the two points at 830.

The threshold value is set by calibration, the value being dependent on the specific hardware that is used. For example, a user with a good bell curve which can be nicely manually observed as in FIG. 8 may set an exemplary value for the threshold.

The operation also may calculate the amount of noise on the bell curve at 831 in an embodiment.

The threshold is compared at 840, and if the value is above the threshold, then a healthy indication is outputted at 815. If the value is below the threshold, then an unhealthy indication is provided at 860. This can be done for one or both of bell curve shape and for noise on the bell curve.

Additional details on the indication can also be provided, for example, healthy, medium and poor can be provided by using three different indications on the device. In general, however, a higher value of area under the curve indicates healthier tooth.

In another embodiment, the computer can integrate the sum of the intensity values between the edge reflected wavelength values and compare that with the empirically determined threshold.

In another embodiment, the percentage of noise on the bell curve is also determined, by determining for example a deviation along the path. Noise greater than specified percentage can also be used to provide an indication of an unhealthy tooth, in addition to the area under the bell curve.

The threshold value can be obtained by finding a healthy tooth and characterizing its bell curve, and the amount of noise on a bell curve, such as the tooth shown in FIG. 8A.

Figure 9:
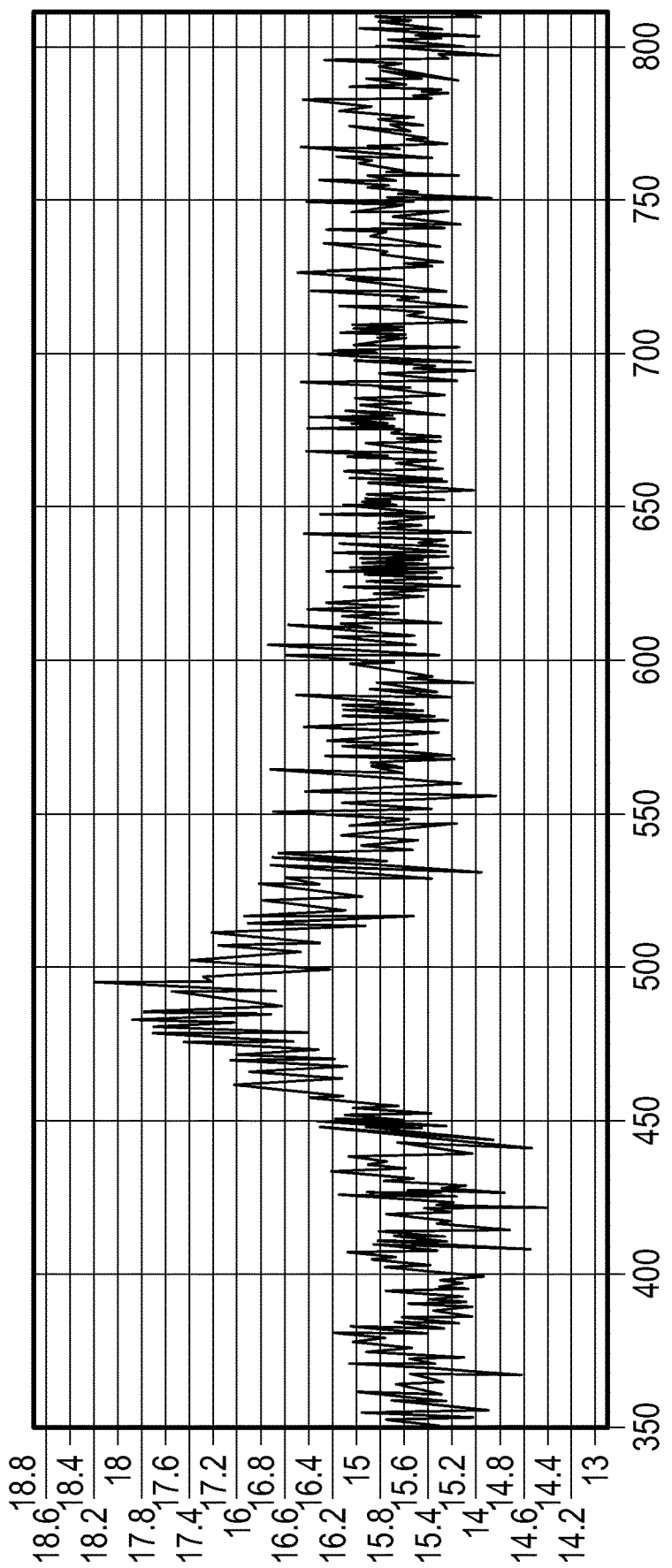
FIG. 9 shows another waveform of the detection peak for incipient caries.

FIG. 9 shows an example of inset of caries, where there is still a peak, but the peak is less pronounced. This can be taken as threshold values for an onset indication, which is displayed as 865. There is also more noise in this part where there is more likely to be insipient caries and the noise value can also be used as part of the comparison with the threshold.

Figure 10:
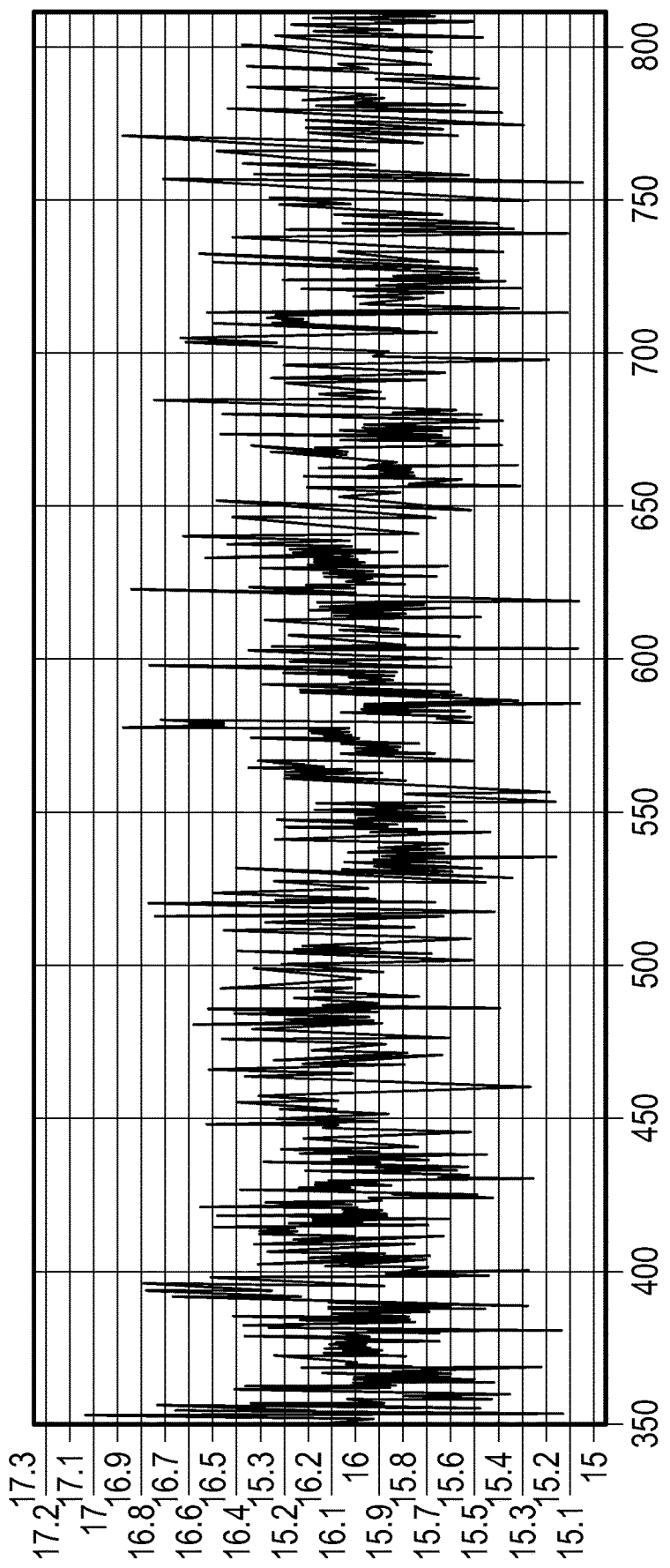
FIG. 10 shows a waveform for late stage caries.

FIG. 10 shows the spectrograph results for late stage caries, showing more noise, and the peak being less pronounced. Values of this type can be used to provide an indication of an unhealthy tooth. In another embodiment, there can be simply a pass fail operation, where the tooth is characterized user is healthy, or as less than healthy which can include either onset or unhealthy indications. In operation, the device is used as a generic toothbrush initially, e.g., an electric toothbrush using the same battery that is used for tooth characterization. Pressing one button activates the electric toothbrush component. Upon completion, another button is pressed to start detection mode, where the laser diodes 205, 206, 207, 208 operate at 405 nm wavelength. Users scan each area of the tooth with the receiving end, pausing for half a second for the spectrometer to quantify the fluorescence intensity of the portion of the tooth being tested. Upon detection of an area of potential enamel/dentinal incipient caries or late stage caries, the LED on the housing illuminates red, whereas detection of sound enamel prompts the LED on the housing to illuminate green.

Another embodiment adds bluetooth connectivity to an app for mobile devices. This app stitches together the different information from both current and previous scans to provide a 3-D model of a user's mouth, with red highlights on specific teeth with potential developing caries. Re-mineralization and demineralization progress could be monitored through the mobile app in this manner.

By using 405 nm lasers to cause the tooth to fluoresce healthy enamel between the ranges of 450 nm-500 nm, feedback on potential caries forming at an early enough stage to reverse through proper hygiene. The 405 nm laser excites disease specific fluorophores, and interacts with both the organic and inorganic matrices within healthy enamel and dentin, causing healthy enamel to produce an autofluorescent spectrum.

As dental caries or cavities begin to progress, calcium bonds and hydroxyapatite begin to degrade and the structure of the enamel and dentin changes in relation to the healthy enamel surrounding the carious lesion.

This causes afflicted areas in enamel to not fluoresce at the same intensity as healthy enamel once excited by a 405 nm laser, even in the earliest stages of caries formation otherwise known as "incipient" caries or "white-spot lesions." At this stage, the caries is rarely visible to the naked eye or dental radiographs, however can be reversed with proper methods of remineralization and increased hygiene in those specific areas.

A preferred way of using this system is to use this invention is as part of the user's nightly oral hygiene routine. A quick but thorough scan right after brushing would enable users to monitor areas that are becoming demineralized and what to watch out for. In one embodiment, the device has the capability to diagnose and even differentiate between different stages of caries. In other embodiments, the embodiment does not make any diagnosis directly, and only notify the user that an area of progressing demineralization has been found and that they should make an appointment with their dentist to get a formal diagnosis. In this manner, using this toothbrush/device is similar to at-home kits for diagnosing other medical diseases such as colon cancer. Integrating the use of this device with a mobile app would allow for data storage of the nightly scans for demineralization. Using the collected historical data, trendlines, charts/graphs, and demineralization progression could be created and tracked on a weekly or monthly basis. A mobile app would further enhance the preventative dentistry ecosystem by involving the dentists, where they are able to see the historical data and trendlines, and provide feedback on where and how to correct any red flags they see and remind users of their oral hygiene routines.

The present device can operate to monitor teeth demineralization in an analogous way to a blood glucose monitoring for diabetes management; and blood pressure measurement devices monitoring for hypertension.

Features we believe are new include the display, here an RGB light, on the housing of a toothbrush providing users with feedback about incipient caries.

Another feature that is believe new is the use of an integrated spectrometer within a toothbrush for caries detection.

Using bluetooth connection to a mobile app to use saved data to create trend-lines and charts reflecting user oral health.

Advantages include the following. This system empowers consumers by providing the means to both monitor and prevent one of the most prevalent chronic illnesses nationally and globally.

Much more cost effective device that provides science previously exclusive to dentists to the average consumer.

Ability to detect caries formation and demineralization at the earliest stages allows users to actively take steps to remineralize those areas, saving thousands in potential restorative procedure costs had they not known something was forming at that location.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A combination toothbrush and tooth detecting system, comprising:
   a housing, having at least one button, and at least one feedback mechanism on the housing which provides feedback to a user indicative of tooth decay and which provides a green indication for a healthy tooth, and provides a red indication for an unhealthy tooth,
   the housing having a top portion which includes multiple emitting lasers which emits a laser light at 405 nm, and the top portion also includes a connection to a bristle system used to brush a user's teeth;
   a receiver, inside the bristle system,
   where the receiver includes an optical long pass filter that removes light below 455 nm;
   and where the receiver receives a received reemission from a user's tooth that is produced by the laser light emitting from the emitting laser, reflected from the user's tooth, and long pass filtered by the optical long pass filter;
   where the bristle system includes an open area surrounded by the bristles,
   where the multiple emitting lasers are located in the open area, surrounded by the bristles of the bristle system, and where the receiver is inside the open area surrounded by the bristles, and;
   an optical connection, coupled to receive the received reemission from the user's teeth from a direction of the bristles and to conduct the received reemission from the receiver, where the optical connection is surrounded by the multiple emitting lasers, with four emitting lasers surrounding the optical connection; and
   a processor, receiving the received reemission from the receiver, and processing a signal within the received reemission to determine information about the reemission from the user's tooth, to determine an amount of tooth decay on a specific tooth,
   wherein the processor includes a spectrometer that produces an output indicating an amount of reemission as a function of wavelength of the reemission in a band of wavelengths for the reemission and creating an output that indicates to the feedback mechanism whether the specific tooth is healthy, wherein the processor characterizes the output from the spectrometer to determine an amount of noise from the spectrometer, and determines health of the tooth using said noise, where less noise indicates better tooth health.

2. The system as in claim 1, wherein the processor characterizes the output from the spectrometer, to determine a health of the tooth by characterizing a bell curve of the amount of reemission, wherein a taller bell curve indicates better tooth health.

3. A combination toothbrush and tooth detecting system, comprising:

a housing, having at least one button, and at least one feedback mechanism on the housing which provides feedback to a user indicative of tooth decay and which provides a green indication for a healthy tooth, and provides a red indication for an unhealthy tooth, the housing having a top portion which includes multiple emitting lasers which emits a laser light at 405 nm, and the top portion also includes a connection to a bristle system used to brush a user's teeth;

a receiver, inside the bristle system, where the receiver includes an optical long pass filter that removes light below 455 nm;

and where the receiver receives a received reemission from a user's tooth that is produced by the laser light emitting from the emitting laser, reflected from the user's tooth, and long pass filtered by the optical long pass filter;

where the bristle system includes an open area surrounded by the bristles, where the multiple emitting lasers are located in the open area, surrounded by the bristles of the bristle system, and where the receiver is inside the open area surrounded by the bristles, and;

an optical connection, coupled to receive the received reemission from the user's teeth from a direction of the bristles and to conduct the received reemission from the receive where the optical connection is surrounded by the multiple emitting lasers, with four emitting lasers surrounding the optical connection; and a processor, receiving the received reemission from the receiver, and processing a signal within the received reemission to determine information about the reemission from the user's tooth, to determine an amount of tooth decay on a specific tooth, wherein the processor includes a spectrometer that produces an output indicating an amount of reemission as a function of wavelength of the reemission in a band of wavelengths for the reemission and creating an output that indicates to the feedback mechanism whether the specific tooth is healthy, wherein the processor integrates a sum of intensity values of the output and compares that with a threshold to determine the health of the tooth by comparing the sum of the intensity values with the threshold.

4. The system as in claim 1, wherein the bristle system covers the receiver, and includes an opening in a shaft of the bristle system through which the reemission is received.

5. The system as in claim 1, wherein the bristle system covers the receiver, and includes an opening in the bristle system through which the reemission is received.

* * * * *